United States Patent
Raymond-Coblantz

(10) Patent No.: US 8,986,755 B1
(45) Date of Patent: Mar. 24, 2015

(54) SKIN MOISTURIZER

(71) Applicant: Sherry May Raymond-Coblantz, Bend, OR (US)

(72) Inventor: Sherry May Raymond-Coblantz, Bend, OR (US)

(*) Notice: Subject to any disclaimer, the term of this patent is extended or adjusted under 35 U.S.C. 154(b) by 0 days.

(21) Appl. No.: 14/098,374

(22) Filed: Dec. 5, 2013

(51) Int. Cl.
| | |
|---|---|
| A61K 36/185 | (2006.01) |
| A61K 36/82 | (2006.01) |
| A61K 36/53 | (2006.01) |
| A61K 8/97 | (2006.01) |
| A61Q 19/08 | (2006.01) |
| A61Q 19/00 | (2006.01) |
| A61K 8/55 | (2006.01) |
| A61K 8/49 | (2006.01) |

(52) U.S. Cl.
CPC . *A61K 8/97* (2013.01); *A61Q 19/08* (2013.01); *A61Q 19/004* (2013.01); *A61K 8/553* (2013.01); *A61K 8/498* (2013.01); *A61Q 19/00* (2013.01)
USPC ............ 424/729; 424/725; 424/745; 424/774; 424/776

(58) Field of Classification Search
CPC ...... A61K 36/185; A61K 36/82; A61K 36/53
USPC .......................... 424/725, 729, 745, 774, 776
See application file for complete search history.

(56) References Cited

U.S. PATENT DOCUMENTS

| | | | | |
|---|---|---|---|---|
| 2008/0107743 A1 * | 5/2008 | Kligerman et al. | ............ | 424/489 |
| 2009/0197840 A1 * | 8/2009 | Kligerman et al. | ............ | 514/129 |

FOREIGN PATENT DOCUMENTS

| | | | | |
|---|---|---|---|---|
| CN | 102908283 A | * | 2/2013 | |
| CN | 102920645 A | * | 2/2013 | |
| CN | 103099756 A | * | 5/2013 | |
| FR | 002845594 A1 | * | 4/2004 | |
| JP | 09301821 A | * | 11/1997 | |
| JP | 02005194208 A | * | 7/2005 | |
| JP | 2013006790 A | * | 1/2013 | |
| RO | 116865 B | * | 7/2001 | |
| WO | WO2006000196 A1 | * | 1/2006 | |

* cited by examiner

*Primary Examiner* — Chris R Tate
*Assistant Examiner* — Randall Winston
(74) *Attorney, Agent, or Firm* — Klarquist Sparkman, LLP.

(57) ABSTRACT

An organic skin moisturizer, which extends and improves the skin cells life cycle, comprised of Sea Buckthorn seed oil, Camellia seed oil, Argan seed oil, Pomegranate seed oil, Meadowfoam seed oil, d-alpha tocopherol, Lecithin oil, Rosemary essential oil, Tea Tree oil, Helichrysum oil, and Coffee Arabica oil. The oils are blended together resulting in a compound that is easily applied to the skin for superior results to keep the skin cells healthier longer. This compound was created to address the Hayflick limit, which is that all skin cells can only divide a specific number of times before the skin cell dies.

1 Claim, No Drawings

SKIN MOISTURIZER

CROSS-REFERENCE TO RELATED APPLICATIONS

None.

STATEMENT REGARDING FEDERALLY SPONSORED RESEARCH OR DEVELOPMENT

None.

BACKGROUND OF THE INVENTION

The present invention relates to a composition for application on the skin for the treatment of wrinkled, damaged and dry skin. The composition has been found to be especially effective against skin blemishes, rosacea, eczema, wrinkles, dryness and contains properties of stimulation to tissue regeneration and epithelial healing with analgesic and anti-inflammation and anti-fungal effects but without leaving scars. The composition is a most welcome remedy for burn, cuts, frostbites, and sores. This anti-aging formula has been used to produce soft moist skin and can be used on an everyday basis without any negative affects on the skin or body. The composition promotes a firmness to the skin and dermal hydration.

There are many products and formulas for treating dry rough skin and just as many formulas to fight wrinkles. The prior art is replete with products and patents claiming skin protection and salvations for aging skin however the present invention combines a combination of organic ingredients for treating various skin disorders that is unique and effective in bringing about soft, moist skin and reducing wrinkles without harming the skin or the body.

Skin disorders, as the term is used herein, encompasses numerous skin conditions ranging in severity from severe dermatitis, severe dry skin, psoriasis, rosacea and other skin blemishes to less severe conditions, such as lack of adequate skin firmness, dermal hydration or scaling, which are nonetheless unsightly and may cause physical discomfort.

Until now, the treatment of skin disorders has been largely based on non-specific drugs, and only limited success has been achieved. Dermatitis, for example, which may be accompanied by severe scaling, fissures, edema, oozing, erosion, itching and thickening of the skin, commonly has been treated with corticosteroids. Such compounds provide symptomatic relief for some patients. Steroids, however, are known to produce many local and systemic side effects, and their long term use may not be desirable.

Similarly Vitamin D is therapeutically effective in treating certain skin disorders, but only in dosages which are associated with undesirable side effects. Vitamin D at the dose ranges used in currently marketed topical preparations is not therapeutically effective against contact dermatitis. Other formulations for treating skin disorders have either been ineffective or have caused significant irritation to the skin Several formulations have been proposed to overcome the disadvantages of the prior art, both for treating skin disorders, and for use in cosmetics in order to prevent skin irritation and clear blemishes.

There are numerous patents issued for the care and condition of skin Each patent uses a variety of ingredients with the combination providing some form of skin treatment. The list is exhaustive, and includes such patents as: U.S. Pat. No. 7,306,810 issued Dec. 11, 2007 to Spencer discloses a skin cream which comprises at least one anti-oxidant, an anti-inflammatory agent, an exfoliant, and an agent to protect against UV irradiation and the cream is made from either oils or creams to promote adsorption of the active ingredients and to increase vibrancy of the skin tone. U.S. Pat. No. 6,281,236 issued Aug. 28, 2001 to Farber discloses a skin cream composition containing allantoin and an emulsifier with improved stability coming from the adjustment of the pH to a range of 4.5 to 5.8. The lower pH preserves the stability of the allantoin and the functionality of the emulsifier system is maintained. 6,572,868, issued Jun. 3, 2003 to Sandra E. Cope, discloses a restructuring complex for cosmetic compositions. The composition comprises safe and effective amounts of carrageenans, borage seed oil, squalane, ceramide 3, ceramide 6, red algae extract, dipalmitoyl hydroxproline, and oleuropein. U.S. Pat. No. 6,193,987, issued Feb. 27, 2001 to M. H. Harbeck, discloses a lubricating composition for the hands and skin. The composition has as its constituents a mixture of organic safflower oil, flaxseed oil, tincture of benzoin, and organic beeswax. And, U.S. Pat. No. 6,479,043, issued Nov. 12, 2002 to Tietjen et al., discloses a depilatory composition. The composition includes emollients, skin conditioners, buffering agents, viscosity increasing agents, emulsion stabilizers, pH adjusters, chelating agents, fragrance, color, lubricants, propellants, or biological agents.

Various topical formulations and oral regimens of vitamins and herbs have been proposed for the treatment of skin conditions. U.S. Pat. No. 6,228,387, issued May 8, 2001 to M. Borod, describes a first composition for topical application and a second composition for oral administration for the treatment of hemorrhoids. The topical composition includes several herbs and vitamins, including grape seed extract and vitamin E, and in one embodiment, a few drops of Essential Oil of Chamomile. Vitamin E occurs naturally as a mixture of tocopherols, the most active being a-tocopherol, used externally, vitamin E is healing to the skin, being used for protection from sun damage, reducing facial lines and wrinkles, and improving skin smoothness, being used as an additive to massage oils and face creams.

In the prior art, there is little or no distinction between the production of the various compound used in the numerous skin treatments. The present invention provides for a combination of organic ingredients blended from various oils, waxes, extracts, and powders to provide for an extended cell life cycle which makes it an exceptional anti-wrinkle formula that can be used everyday with no adverse side effects. It was created to extend the skin cell's life cycle. The use of organic products, including wild crafted products eliminates additives such as synthetic preservatives and ingredients treated with chemical fertilizers. The products used in the blended compound do not contain genetically modified organisms, and are not processed using irradiation, industrial solvents, dyes, or chemical food additives. The combination of products has been found to produce a synergistic effect, increasing the useful properties of the individual compounds. By eliminating products that are made or produced with pesticides, genetically altered organisms or chemical fertilizers the effects of the product are enhanced and this limits any potential harmful side effects to the skin

BRIEF SUMMARY OF THE INVENTION

An organic skin moisturizer, which extends and improves the skin cells life cycle, comprised of Sea Buckthorn seed oil, Camellia seed oil, Argan seed oil, Pomegranate seed oil, Meadowfoam seed oil, d-alpha tocopherol, Lecithin oil, Rosemary essential oil, Tea Tree oil, Helichrysum oil, and Coffee Arabica oil. The oils are blended together resulting in a compound that is easily applied to the skin for superior results to keep the skin cells healthier longer. This compound was created to address the Hayflick limit, which is that all skin cells can only divide a specific number of times before the skin cell dies. Recent evidence indicates that caffeine and caffeine sodium benzoate, found in Coffee Arabica oil, may increase UVB-induced apoptosis both in topical and oral applications The various components are mixed together using volume measurements, rather than by weight, to create the skin moisturizer. The various oils, waxes, extracts, and powders are blended in an environment with controlled humidity. Prior to mixing, the components are filtered to eliminate impurities. Application of the moisturizers should be done after the skin has been washed with a hot washcloth. The blended formula is applied to the fingertips or palm and applied in an upward motion or against the grain of the skin. If makeup or sun screen are to be applied after application of the moisturizer, then wait approximately 10 to 15 minutes or until the moisturizer has been absorbed by the skin

BRIEF DESCRIPTION OF THE SEVERAL VIEWS OF THE DRAWING

None

DETAILED DESCRIPTION OF THE INVENTION

Various embodiments of the invention will now be described. The following descriptions provide specific details for a thorough understanding and enabling description of these embodiments. Additionally, some well-known structures or functions may not be shown or described in detail, so as to avoid unnecessarily obscuring the relevant description of the various aspects and embodiments of the invention.

The terminology used in the description presented below is intended to be interpreted in its broadest reasonable manner, even though it is being used in conjunction with a detailed description of certain specific embodiments of the invention. Certain terms may even be emphasized herein; however, any terminology intended to be interpreted in any restricted manner will be overly and specifically defined as such in this Detailed Description section.

The present invention is a skin moisturizer for repairing the skin, the formula is created by combining many organically or naturally produced ingredients, most all of these ingredients are vegan or plant based and gluten free. The various ingredients are oils, extracts, waxes, and powders that are blended after being filtered to remove any non-essential impurities. The ingredients are checked for radiation by a geiger counter and rejected if they measure above 60 counts per minute. By combining the various ingredients a catalytic reaction is created that the applicant has discovered improves the user's skin significantly. The skin is more youthful, firmer, softer and shows fewer wrinkles. The present invention is a topical skin treatment that reduces dryness, tightens the pores and reduces wrinkles. The present invention is beneficial to sunburned skin, radiated skin or skin with blemishes due to harsh environments, such as sun, wind, extreme cold and other skin conditions. The present invention produces a firmer tighter skin which results in a softer skin with fewer wrinkles.

The present invention is an emulsion and is not a water based moisturizer. The blended moisturizer discussed below uses primarily carrier and essential oils. The blending of the two types of oils allows for the mixture to be more readily absorbed into the skin. The ingredients in the moisturizers described below are vegan and gluten free and made from natures finest quality organic ingredients using only organic processing.

The moisturizers are produced using organic products, which means: the ingredients are grown and processed organically. For example, organic farming practices are designed to encourage soil and water conservation and reduce pollution. Farmers who grow organic produce don't use conventional methods to fertilize or control weeds. For example, rather than using chemical weed killers, organic farmers may conduct more sophisticated crop rotations and spread mulch or manure to keep weeds at bay. Additionally, the ingredients are organically processed which includes; cold press extraction or other means for processing the various plants to produces the oils without using or adding chemicals in the extraction process. The following moisturizers were developed using organic or natural ingredients and have produced exceptional results. The claims are not limited to organic ingredients but the applicant cannot confirm the same positive results using non-organic products.

Most of the blended oils of the present invention are either designated essential oils or carrier oils. Essential oils are extracts from the petals, root, bark, stem, leaves and aromatic portions of the plant. There are several extraction methods in practice like the steam distillation method, cold-pressing method and solvent extraction method. These essential oils are thin oils with strong aromas. They evaporate quickly and generally absorb quickly into the skin. The essential oils used in the present compound include, Rosemary essential oil, Helichrysum oil, Tea Tree oil, and Coffee Arabica oil.

Carrier oils, also called fixed oils, are vegetable oils that are used to dilute essential oils. Since essential oils can cause skin irritations or itching when used in undiluted forms. Carrier oils are used as base oils to dilute essential oils for maximum effectiveness. In the present compounds, the following oils are carrier oils; sea buckthorn oil, pomegranate seed oil, argan oil, camellia seed oil, and meadowfoam seed oil. The present invention is formulated by adding the components by volume. Each ingredient has a specified percentage range prescribed below.

The present invention is a skin moisturizer comprised of approximately: 20-35% by volume Sea Buckthorn seed oil, also known as hippohae rhamnoides oil, 17-25% by volume Camellia seed oil also known as Camellia Oleifera seed oil, 15-24% by volume Argan seed oil also known as Argania spinosa nut oil, 5-15% by volume Pomegranate seed oil also known as Punica granatum seed oil, 5-12% by volume Meadowfoam seed oil also known as Limnanthes Alba seed oil, 3-7% by volume Lecithin, the INCI name being Lecithin, 3-7% by volume d-alpha tocopherol, 1-5% by volume Rosemary essential oil also known as Rosmarinu Officinalis, 1-5% by volume Tea Tree oil, the INCI name being Melaleuca Alternifolia Leaf Oil, 1-5% by volume Helichrysum oil, the INCI name being Helichrysum italicum oil, and less than 2% by volume Coffee Arabica oil.

Each ingredient is listed by their common name or their International Nomenclature of Cosmetic Ingredients, abbreviated INCI wherever possible. The INCI is a system of names for waxes, oils, pigments, chemicals, and other ingredients of soaps, cosmetics, and the like, based on scientific names and other Latin and English words The Sea Buckthorn seed oil, the INCI name being Hippohae rhamnioides seed oil, which is derived from the seed of the Hippophae rhamnoides, a plant or shrub found throughout Europe and Asia. The oil is produced by cold press of the seeds and only the seeds which produces a number of fatty acids, including; Beta Carotene, Lycopene, Linoleic, Oleic, Palmitic, Palmitoleic, and Stearic acids. In addition to being used as a conditioning oil it is also beneficial in the treatment of burns, wounds, lesions, and sun damaged skin.

The Camellia seed oil, the INCI name being Camellia Oleifera seed oil, is a highly penetrating and almost odorless oil, there is a very slight herbal aroma. It is virtually clear with a slight yellow hue. Camellia Oil is light in texture and absorbs quickly into the skin Approximately 85% of the fatty acid composition contained in Camellia Oil is in the form of monounsaturated oleic acid. Camellia Oil is also a rich source of other omega 3,6 and 9 fatty acids and polyphenols. The Camellia seed oil has been shown to have the following properties; penetrates quickly, moisturizes, emits a light herbal aroma, is rich in fatty and essential fatty acids, contains tocopherol a form of Vitamin E, and contains an abundance of polyphenols.

The Argan oil, the INCI name being Argania spinosa nut oil, is an oil produced from the kernels of the Argan tree, found primarily in Morocco. The oil is valued for its nutritive, cosmetic and numerous medicinal properties. Argan oil remains one of the rarest oils in the world due to the small and very specific growing areas. The oil contains a number of fatty acids, including; Palmitic, Stearic, Oleic, Linoleic, and Linolenic acid. The oil is exceptionally rich in natural tocopherols, phenols and phenolic acid, carotenes, squalene, essential fatty acids, 80% unsaturated fatty acids. The composition of the Argan oil makes it resistant to oxidation and therefore a stabilizer for the blended oils.

Pomegranate seed oil, the NCI name being Punica granatum seed oil, which is commonly used in cosmetic products to revitalize dull or mature skin, assist with wrinkles, and to soothe minor skin irritations. It provides relief from minor skin irritations and inflammation, including dry skin, eczema, psoriasis and sunburned skin. The conjugated fatty acids give it strong anti-inflammatory properties, which help to reduce swelling and ease muscular aches and pains. Several recent studies have shown that pomegranate seed oil stimulates keratinocyte proliferation, promoting regeneration and strengthening of the epidermis. The oil contains more than 60% puninic acid, a valuable conjugated linolenic acid. Additional ingredients of the Pomegranate seed oil, include tocopherols, sterols and a small amount of squalene.

Meadowfoam seed oil, the NCI name being Limnanthes alba seed oil, is extracted from the seeds of Limnanthes alba (meadowfoam). The seeds contain 20-30% oil. Meadowfoam seed oil is extraordinarily stable, primarily because it contains over 98% long chain fatty acids. Meadowfoam oil is used in cosmetic and hair-care applications due to its stability, lubricity and ability to stay on the skin.

The d-alpha tochopherol is commonly known as Vitamin E derived from vegetable oil and is used in various skin treatment compound. D-alpha-tocopherol is an important lipid-soluble antioxidant and it protects cell membranes from oxidation by reacting with lipid radicals produced in the lipid peroxidation chain reaction. This process helps in removing free radical intermediates and prevent the oxidation reaction from continuing. The oxidized d-alpha-tocopheroxyl radicals produced in this process may be recycled back to the active reduced form through reduction by other antioxidants, such as ascorbate, retinol or ubiquinol.

Lecithin, the INCI name being Lecithin, can easily be extracted chemically or mechanically. It is usually available from sources such as soybeans, rapeseed, cottonseed, and sunflower. It has low solubility in water, but is an excellent emulsifier.

Rosemary essential oil, the INCI name being Rosmarinu Officinalis, improves circulation and has a rejuvenating effect on the skin Rosemary is a common ingredient used in many cosmetics, including skin toners, creams, soaps and hair products. The essential oil is known to assist in the prevention of age-related skin damage, such as wrinkles. The oil is derived from the flowering top of the plant. Organic extraction requires steam distillation of the oil from the plant. The Rosemary essential oil is derived from the plant Rosmarinus Officinalis, a perennial herb plant with small and slender evergreen needle like leaves, and white, pink, purple, or blue flowers, native to the Mediterranean region.

The Tea Tree oil, the INCI name being Melaleuca Alternifolia Leaf Oil, contributes to the stability of the blended oils and are high in antioxidants.

Helichrysum oil, the INCI name being Helichrysum italicum oil, which has properties that are beneficial to the skin, including; acting as an anti-inflammatory and soothes burns and raw chapped skin. It is used as a stabilizing and preserving agent in the present compound as well as a contributing to the benefits to the skin Helichrysum has been used in Europe for its healing qualities for over a millenia and is known as "immortelle" oil.

The Coffee Arabica oil, the NCI name being coffee arabica oil, is derived from the small seeds of the coffee nut or bean—the size of the seed is rather small and it takes quite a large number of seeds to produce usable amounts. The oil is generally separated from the seed using a cold press method, but there are other methods for extraction.

I claim:
1. An emulsion for moisturizing skin comprising:
   20-35% by volume Sea Buckthorn seed oil, the INCI name being hippohae rhamnoides oil;
   17-25% by volume Camellia seed oil, the INCI name being Camellia Oleifera seed oil;
   15-24% by volume Argan seed oil, the INCI name being Argania Spinosa nut oil;
   5-15% by volume Pomegranate seed oil, the INCI name being Punica granatum seed oil;
   5-12% by volume Meadowfoam seed oil, the INCI name being Limnanthes alba seed oil;
   3-7% by volume Vitamin E, the INCI, name being d-alpha tocopherol;
   3-7% by volume Lecithin, the INCI name being Lecithin;
   1-5% by volume Rosemary essential oil, the INCI name being Rosmarinu Officinalis;
   1-5% by volume Tea Tree oil, the INCI name being Melaleuca Alternifolia Leaf Oil;
   1-5% by volume Helichrysum oil, the INCI name being Helichrysum italicum oil; and
   Less than 2% by volume Coffee Arabica oil, the INCI name being Coffee Arabica.

* * * * *